US008055055B2

(12) United States Patent
Hamada et al.

(10) Patent No.: US 8,055,055 B2
(45) Date of Patent: Nov. 8, 2011

(54) METHOD FOR INSPECTING A FOREIGN MATTER ON MIRROR-FINISHED SUBSTRATE

(75) Inventors: Taizou Hamada, Osaka (JP); Tatsutoshi Suenaga, Osaka (JP)

(73) Assignee: Panasonic Corporation, Osaka (JP)

( * ) Notice: Subject to any disclaimer, the term of this patent is extended or adjusted under 35 U.S.C. 154(b) by 1054 days.

(21) Appl. No.: 11/911,594

(22) PCT Filed: Apr. 19, 2006

(86) PCT No.: PCT/JP2006/308172
§ 371 (c)(1),
(2), (4) Date: Oct. 15, 2007

(87) PCT Pub. No.: WO2006/112466
PCT Pub. Date: Oct. 26, 2006

(65) Prior Publication Data
US 2009/0034829 A1    Feb. 5, 2009

(30) Foreign Application Priority Data

Apr. 19, 2005  (JP) ................. 2005-120569

(51) Int. Cl.
*G06K 9/00* (2006.01)
(52) U.S. Cl. ........ 382/141; 382/144; 382/145; 382/146; 382/147
(58) Field of Classification Search ........... 382/141–152
See application file for complete search history.

(56) References Cited

U.S. PATENT DOCUMENTS

| 6,356,300 B1 * | 3/2002 | Shiba ............................ 348/130 |
| 6,621,928 B1 * | 9/2003 | Inagaki et al. ................. 382/199 |
| 2001/0042068 A1 | 11/2001 | Yoshida et al. |
| 2004/0156539 A1 | 8/2004 | Jansson et al. |

FOREIGN PATENT DOCUMENTS

| JP | 03-095404 A | 4/1991 |
| JP | 3-95404 A | 4/1991 |
| JP | 05-071934 A | 3/1993 |
| JP | 06-302676 A | 10/1994 |
| JP | 09-133636 | 5/1997 |
| JP | 10-040544 | 2/1998 |
| JP | 11-023414 | 1/1999 |
| JP | 2000-046537 | 2/2000 |

(Continued)

OTHER PUBLICATIONS

Chinese Office Action dated Sep. 25, 2009.

(Continued)

*Primary Examiner* — Brian Le
(74) *Attorney, Agent, or Firm* — RatnerPrestia

(57) ABSTRACT

Provided is a foreign matter inspection method for positively detecting a foreign matter in the neighborhood of the edge of a mirror-finished substrate without fail. Edge-emphasis and binarization are performed following the taking of an image of a substrate-under-inspection at a contour of its inspection area, to further detect a plurality of sampling points representative of a contour of the inspection area. An estimated inspection area is determined by determining the size, position and rotation angle of contour lines defined, size-reducibly, from the coordinates of the plurality of sampling points. After applying a mask to the binary image data in an area other than the estimated inspection area, a foreign-matter detection step is performed.

6 Claims, 14 Drawing Sheets

FOREIGN PATENT DOCUMENTS

| | | |
|---|---|---|
| JP | 2000-329532 A | 11/2000 |
| JP | 2001-266142 | 9/2001 |
| JP | 2002-334430 A | 11/2002 |
| JP | 2003-004428 A | 1/2003 |
| JP | 2004-309460 A | 11/2004 |
| JP | 2006-064975 | 3/2006 |
| JP | 2007-528161 | 1/2011 |
| JP | 2007-528161 | 4/2011 |

OTHER PUBLICATIONS

International Search Report for Application No. PCT/JP2006/308172, dated May 23, 2006.

\* cited by examiner

METHOD FOR INSPECTING A FOREIGN MATTER ON MIRROR-FINISHED SUBSTRATE This application is a U.S. National Phase Application of PCT International Application PCT/JP2006/308172.

TECHNICAL FIELD

The present invention relates to a foreign matter inspection method that inspects a projection or foreign matter on an object surface by emitting light to an object surface and detecting the reflection light thereof, and more particularly to a foreign matter inspection method on mirror-finished substrate, e.g. a hard disk substrate or a semiconductor silicon wafer.

BACKGROUND ART

Recently, the hard disk drive, representative of a magnetic disk device, is in a conspicuous trend toward the increase of recording density in order to realize small size and large capacity, whose track width is reduced down to 1 µm or smaller. In order for the head to correctly scan over such a narrow track, the head-tracking servo technology plays an important role. The presently available hard disk drive, using such track servo art, is to record a tracking servo signal, an address information signal, a reproducing clock signal, etc. at a constant angular interval in one turn of the disk. The drive device is to detect and rectify the head position according to those signals reproduced at a constant time interval from the head, thus allowing the head to correctly scan over the track.

Because the servo signal, the address information signal, the reproducing clock signal, etc. serve as reference signals for the head to correctly scan over the track, high positioning accuracy is required in the writing thereof (hereinafter, described "formatting"). In the presently available hard disk drive, formatting is performed by positioning in position the recording head with use of an exclusive servo device built with an accurate position detector utilizing light interference (hereinafter, referred to as a servo writer).

However, the following disadvantages exist in the formatting by means of the foregoing servo writer. Firstly, much time is required in writing signals over a multiplicity of tracks while accurately positioning the head in position. Thus, there is a need to operate many servo writers simultaneously in order to improve productivity. Secondly, a great deal of cost is needed in introducing many servo writers and maintaining/managing those. Such disadvantages are more serious as track density improves and track count increases.

In this situation, there is proposed a scheme and magnetic transfer apparatus that, by superimposing a disk called a master previously written with all pieces of servo information with a magnetic disk requiring formatting and then externally providing transfer energy to those, the information on the master is transferred in batch to the magnetic disk without using a servo writer in formatting (e.g. Japanese Patent Unexamined Publication No. H10-40544).

In the proposal, the substrate has a surface on which a magnetic region of ferromagnetic material is formed in a patterned form for information signals, thus being made as a magnetic transfer master. The magnetic transfer master at its surface is placed in contact with a surface of a sheet-formed or disk-like magnetic recording medium formed with a ferromagnetic thin film or ferromagnetic powder-applied layer, to which predetermined magnetic field is applied. Due to this, the method allows the magnetic recording medium to record a magnetized pattern having a patterned form corresponding to the information signal formed on the magnetic transfer master.

In the magnetic transfer device for use in the formatting according to the foregoing magnetic transfer scheme, formatting is available instantaneously. Nevertheless, in order to obtain preferable magnetic transfer signal quality, there is a need to place the magnetic transfer master and the magnetic disk in close contact with each other without any gap at the entire surfaces. For this purpose, it is significantly important to control the foreign matters and projections existing on a magnetic transfer master surface or a magnetic disk surface. Particularly, for the magnetic disk for magnetic transfer, it is vital to conduct a foreign-matter inspection without fail on the magnetic disk entirely in the planar surface thereof immediately before executing magnetic transfer.

As a foreign-matter inspection apparatus for use in a foreign-matter inspection on a planar region of a magnetic disk, there is known a foreign-matter inspection apparatus that scans a laser spot over a magnetic disk surface and inspects a foreign matter or projection on the magnetic disk by detecting the reflection light thereof (e.g. Japanese Patent Unexamined Publication No. 2003-4428).

FIG. 14 shows a foreign-matter inspection apparatus in the prior art. At the first step, by rotating inspection index 101 120 degrees, magnetic disk 102 to be inspected is transported to an inspection position where magnetic disk 102 lying in an inspection position is vacuum-held by inspection stage 103.

At the second step, the AD conversion board in computer 109 is notified of a sampling start.

At the third step, magnetic disk 102 is rotated by rotation driver 104 through inspection stage 103.

At the fourth step, a predetermined voltage is applied to laser light source 105, to emit laser light L1 to magnetic disk 102 on the inspection stage 103. The reflection light and scattering light of the same is received by light-reception camera 106 so that the image outputted from light-reception camera 106 is fetched to the A/D converter board of within computer 109. From the captured image, a foreign matter is detected by image recognition. This operation is performed several times by changing the laser-light irradiation position radially of the disk.

At the fifth step, laser light L2 is irradiated from dimension-measurer's illuminator 107 and passed through the lateral of an edge of magnetic disk 102. Otherwise, the laser light L2 scattered by the edge is received by dimension-measurer's light receiver 108 so that the A/D converter board in computer 109 can input therein a voltage value dependent upon the light-reception amount corresponding to the edge position.

At the sixth step, after terminating the sampling of voltage values (i.e. edge position measurement) during 360 degree rotation of magnetic disk 102, the voltage-value sampling result inputted to the A/D converter board is taken out to calculate a deviation amount (X, Y) from the setting value (0.0) of a rotating center of magnetic disk 102. At the sixth sequence, after detecting foreign matters on magnetic disk 102 throughout the entire area up to the outermost or the innermost, the deviation amount (X, Y) obtained at the fifth sequence is added to each of the obtained foreign-matter detection data.

Then, checking is made as to whether or not each foreign matter the deviation amount has been added has a coordinate lying inside or outside the inspection area. The detection data of a foreign matter lying outside is considered corresponding to the edge of magnetic disk 102 and excluded from the foreign-matter detection data. In this manner, because inspection is conducted while correctly measuring the outer peripheral edge position of magnetic disk 102, it is possible to exclude a erroneous recognition due to an irregular reflection at the outer peripheral edge. By scanning the laser light L1 up to the outer peripheral edge, foreign-matter detection can be effected thoroughly up to the outer peripheral edge.

However, the conventional foreign-matter inspection method and apparatus is to correctly measure the outer peripheral edge position of the disk, thus being required to use an expensive measuring instrument, such as a laser dimension measuring instrument. This raises a disadvantage of increasing apparatus price. Furthermore, because the disk is usually chamfered at its edge, the planar region to be inspected exists inward by a chamfer dimension from the outer peripheral edge. Generally, chamfer is low in working accuracy wherein chamfer dimension has a larger tolerance. Accordingly, even if the disk outer peripheral edge position is measured correctly, it is not easy to correctly determine a contour of the planar region to be inspected. Due to this, there is disadvantageously an increasing possibility to erroneously recognize the light irregularly reflected by the chamfer of the disk as light reflected from a foreign matter.

DISCLOSURE OF THE INVENTION

Overcoming the foregoing disadvantage, a foreign matter inspection method on mirror-finished substrate in the present invention is to clearly detect a contour of a planar region, to be inspected, of a mirror-finished substrate-under-inspection without using an expensive measuring instrument. There is provided a foreign matter inspection method on mirror-finished substrate which is capable of positively detecting a foreign matter or projection existing on the planar region of a substrate-under-inspection, particularly a foreign matter or projection significantly close to or in contact with a contour of a planar region to be inspected.

In a concrete foreign matter inspection method on mirror-finished substrate, prepared is an image data based on irregular reflection light that has been irregularly reflected from a substrate-under-inspection irradiated with illumination light. Detected are coordinates of a plurality of contour sampling points indicative of a contour of an inspection area, from the image data where the contour of an inspection area of the substrate-under-inspection has been taken an image. Estimated is an inspection area from the coordinates of the plurality of contour sampling points, to prepare mask image data where masking is applied to an area other than the inspection area at the image data, and performing foreign-matter detection on the image data by using of the mask image data.

This method allows for clearly detecting an inspection area of a mirror-finished substrate that is a substrate-under-inspection without using an expensive measuring instrument like a laser dimension measuring instrument. In addition, the foreign matters or projections existing on the mirror-finished surface provided as an inspection area can be positively extracted thoroughly throughout the entire of the inspection area. Particularly, it is possible to clearly clip an image of a foreign matter or projection that is close to or in contact with the contour of the inspection area of the subject-under-inspection. The foreign matter or projection present on the mirror-finished substrate can be detected by a comparatively simple process.

In the method, the image data may be a binary image processed with binarization. This method can eliminate the halo caused by stray light, etc. from the substrate-under-inspection irradiated with illumination light, and clearly detect a foreign matter or projection present at a contour boundary of the inspection area or on the inspection area of the substrate-under-inspection finished as a mirror surface.

In the method, a contour line may be estimated so as to minimize a square sum of distances between coordinates of the plurality of contour sampling points and the contour line of the inspection area of the substrate-under-inspection. This method can establish a contour line of the inspection area of the substrate-under-inspection finished as a mirror surface and make clear the inspection area by generating a binary masking image by use of the contour line.

In the method, a reflection member for irregularly reflecting light or a light-emission member for spontaneously emitting light may be provided in a neighborhood of the substrate-under-inspection, the image data being due to taking an image of the subject-under-inspection in an area broader than the inspection area wherein the image data is produced such that an image of the reflection member or light-emission member is displayed in a background of the substrate-under-inspection.

With this method, even where a chamfer does not exist at an edge of the substrate-under-inspection or it is significantly small, the contour of the mirror-finished surface provided as an inspection area of the substrate-under-inspection is to be displayed clearly, thus making it possible to clip and inspect the image data only at the mirror-finished surface provided as an inspection surface and detect a foreign matter or projection existing on the mirror-finished substrate through a simple process.

A foreign matter inspection method on mirror-finished substrate according to the invention, has a step of converting an image data formed of irregular reflection light from the substrate-under-inspection into a binary image having two values, i.e., a dark-region data value and a light-region data value, through emitting illumination light to the substrate-under-inspection. Extracted is an image data series on a plurality of positions of straight lines radially extending from a center established in the binary image and different in inclination, to inspect sequentially the image data on the respective straight lines in either direction of from an inner periphery to outer periphery of the substrate-under-inspection or a direction from an outer periphery to inner periphery. There are had a step of determining a coordinate of the data at which data value changes as an outer-contour sampling point coordinate on the plurality of straight lines, and a step of determining a center and a radius of an outer contour circle representative of an outer contour of the inspection area of the substrate-under-inspection from the plurality of outer-contour sampling point coordinates. Extracted is an image data series on a plurality of positions of straight lines radially extending from a center established in the binary image and different in inclination, to inspect sequentially the image data series on the respective straight lines in either from an outer periphery to inner periphery of the substrate-under-inspection or a direction from an inner periphery to outer periphery. There is had a step of determining a coordinate of the data at which data value changes as an inner-contour sampling point coordinate on the plurality of straight lines. There is had a step of determining a center and a radius of an inner contour circle representative of an inner contour of the inspection area of the substrate-under-inspection from the plurality of inner-contour sampling point coordinates. There are had a step of generating, for the binary image, a mask image that image data value has been changed to dark-region data value in portions outside of the outer contour circle and inside of the inner contour circle, and a step of detecting image data having a light-region data value from the binary image and the mask image.

The foreign-matter inspection method on mirror-finished substrate can clearly detect an inspection area of a mirror-finished substrate provided as a substrate-under-inspection and positively extract a foreign matter or projection existing on the mirror-finished surface provided as an inspection area thereof thoroughly throughout the entire inspection area. Particularly where there exists a foreign matter close to or in contact with a contour of the inspection area of the substrate-under-inspection, a projection image can be clipped out with clarity. This allows for detecting a foreign matter or projection present on the mirror-finished substrate without using an expensive measuring instrument such as a laser dimension-measuring instrument.

According to the foreign matter inspection method of the invention, inspection can be conducted throughout the entire inspection area because foreign-matter detection is performed after estimating an inspection area by use of the image data the substrate-under-inspection has been taken an image of at a contour of the inspection area and applying an mask to the image data in a portion other than the inspection area. Furthermore, the image of a foreign matter or projection in proximity to or in contact with the contour of the inspection area can be separated from the image of inspection-region contour. Accordingly, the foreign matter present close to the contour can be positively detected, thus providing a great effect that a foreign matter or projection existing on a magnetic disk surface can be inspected without using such an expensive measuring instrument such as a laser dimension-measuring instrument.

DESCRIPTION OF REFERENCE NUMERALS AND SIGNS

Figure 1:
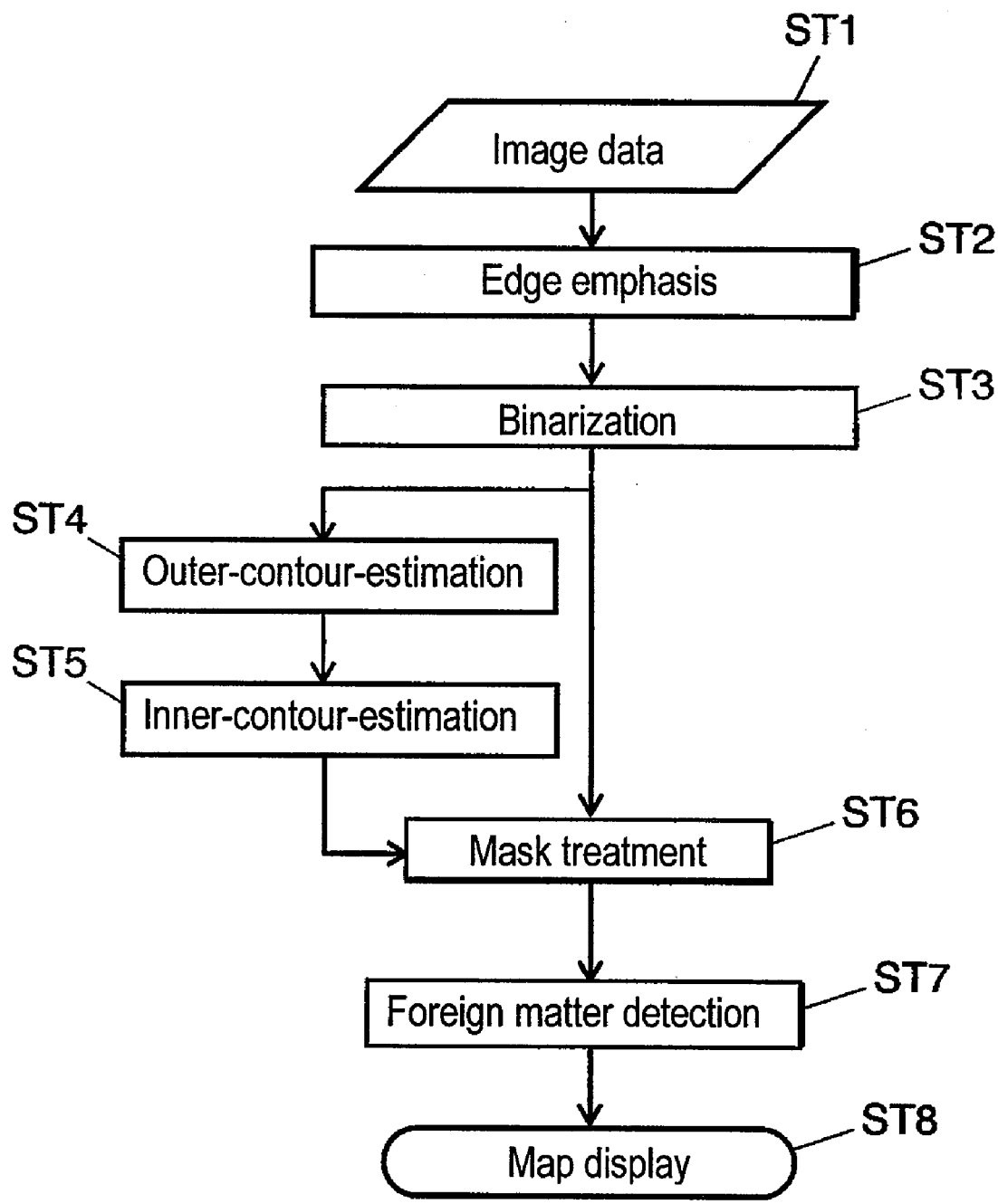
FIG. 1 is a flowchart of a foreign matter inspection method on mirror-finished substrate according to embodiment 1 of the present invention.

9 Imager device
10 Lens
11 LED illuminator
12 Lens barrel
13 Mirror-finished surface
14 Chamfer
15 Foreign matter
16 Irregular reflection plate
101 Inspection index
102 Magnetic disk
103 Inspection stage
104 Rotation driver
105 Laser light source
106 Light-reception camera
107 Dimension-measurer's illuminator
108 Dimension-measurer's light receiver
109 Computer
C1 Outer contour circle
C2 Inner contour circle
DL1-DL8 Sampling directions at outer periphery
DL9-DL16 Sampling directions at inner periphery
E1 Outer contour
E2 Inner contour
L1, L2 Laser light
L3 Illumination light
L4 Regular reflection light
L5 Irregular reflection light
O1 Center
PA1-PA8 Outer-contour sampling points
PA9-PA16 Inner-contour sampling points
Z1, Z2, Z3 Foreign-matter images
Z4, Z5 Reflection-upon-chamfer image
Z6, Z7 Irregular-reflection-plate image

PREFERRED EMBODIMENTS FOR CARRYING OUT THE INVENTION

While referring to the drawings, explanation will be now made on embodiments according to the present invention. Note that the ensuing embodiments are described with a magnetic disk exemplified as a substrate to be inspected. In the drawings, like reference numeral is attached to like element.

Embodiment 1

Figure 2:
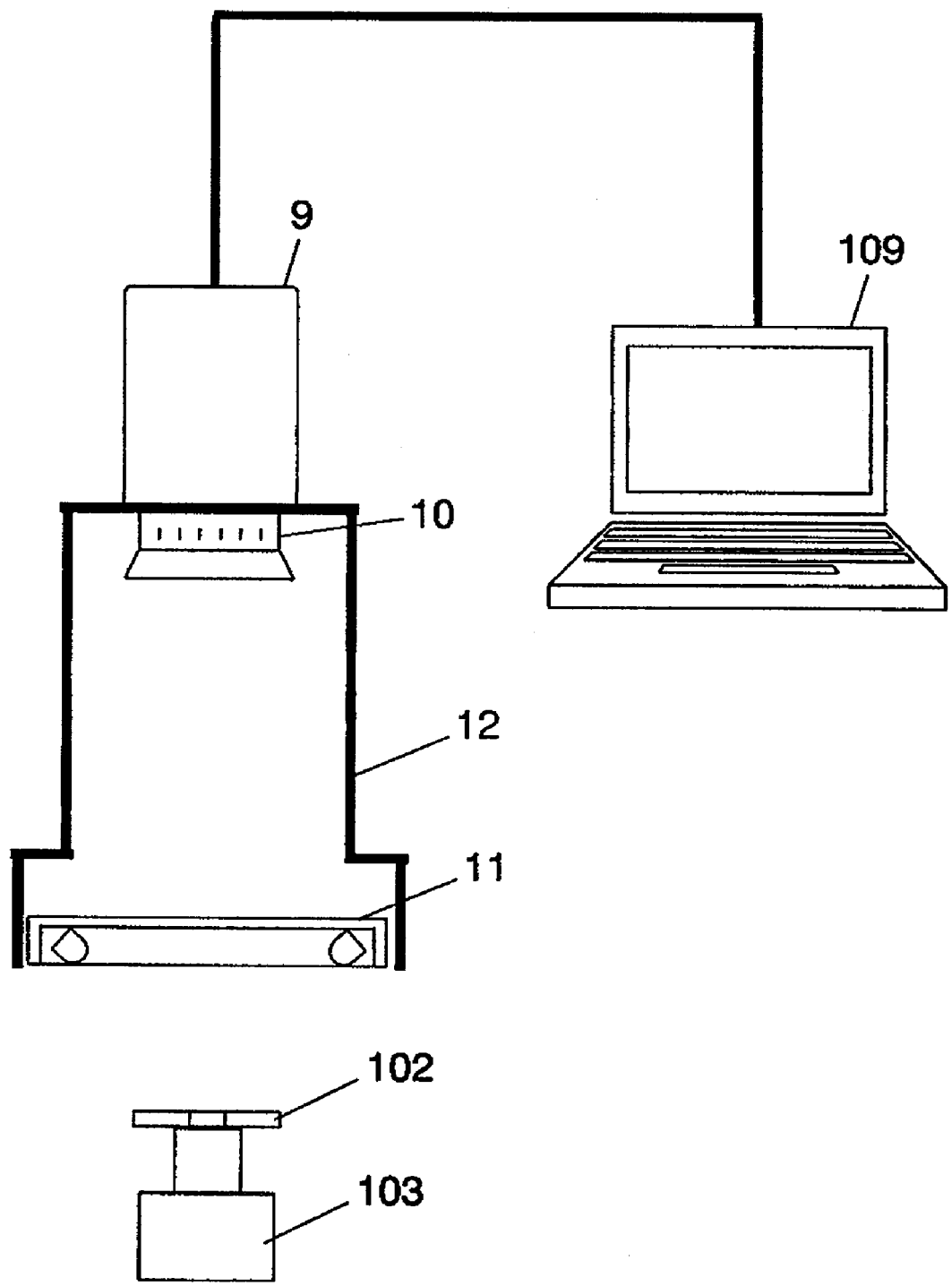
FIG. 2 is a schematic diagram of an inspection apparatus for acquiring image data, in the foreign matter inspection method on mirror-finished substrate according to embodiment 1 of the invention.
Figure 3:
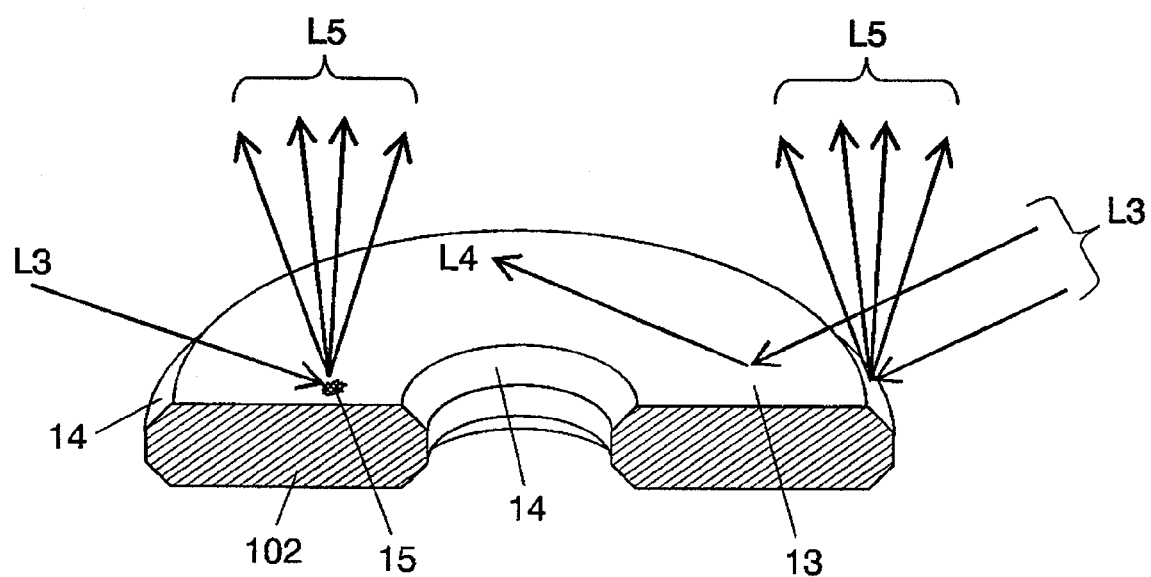
FIG. 3 is a broken-away perspective view for explaining the generation of image data in the inspection apparatus shown in FIG. 2, in the foreign matter inspection method on mirror-finished substrate according to embodiment 1 of the invention.
Figure 4:
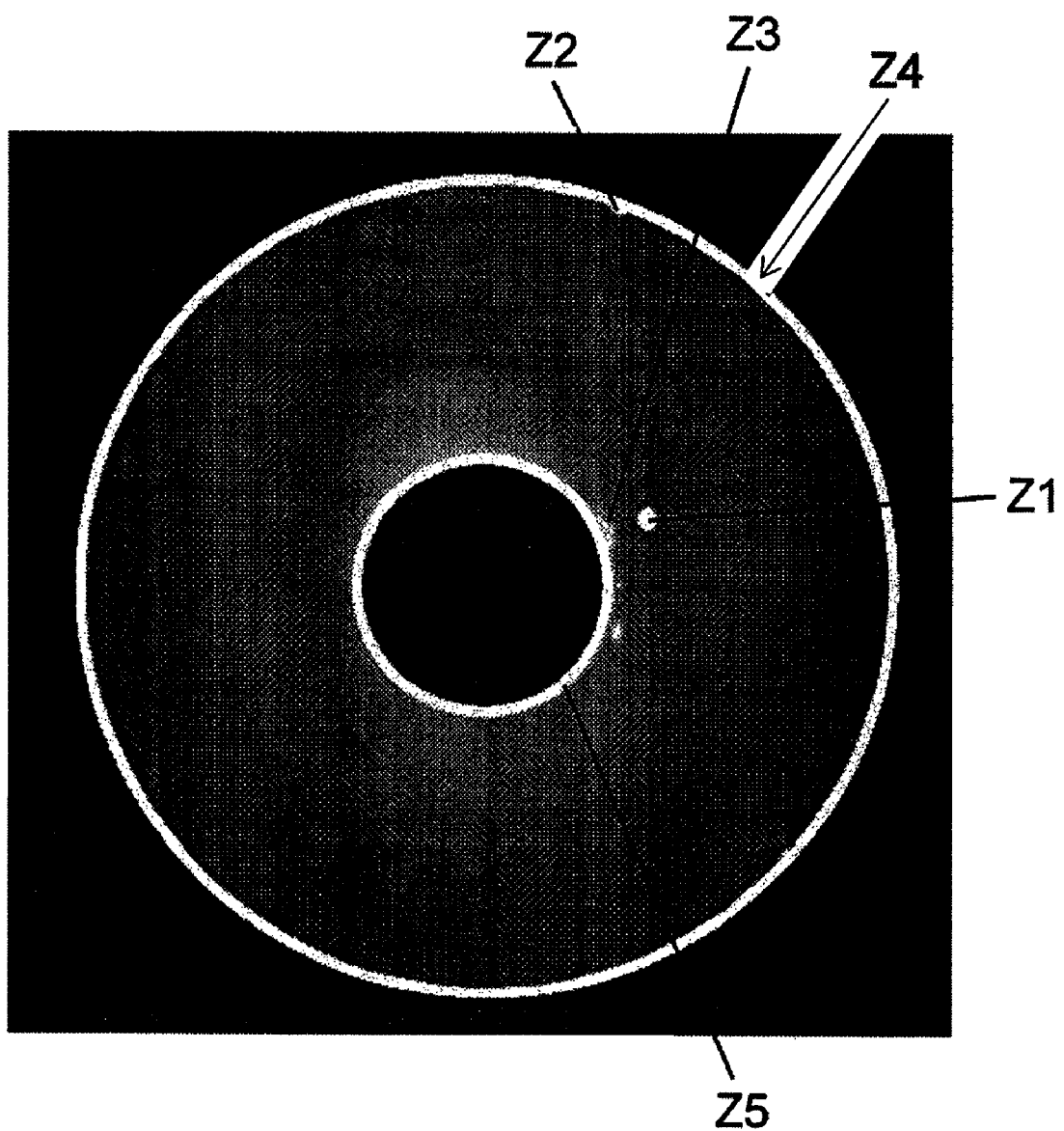
FIG. 4 is a figure showing the image data of a magnetic disk acquired by using the inspection apparatus explained in FIG. 2, in the foreign matter inspection method on mirror-finished substrate according to embodiment 1 of the invention.
Figure 5:
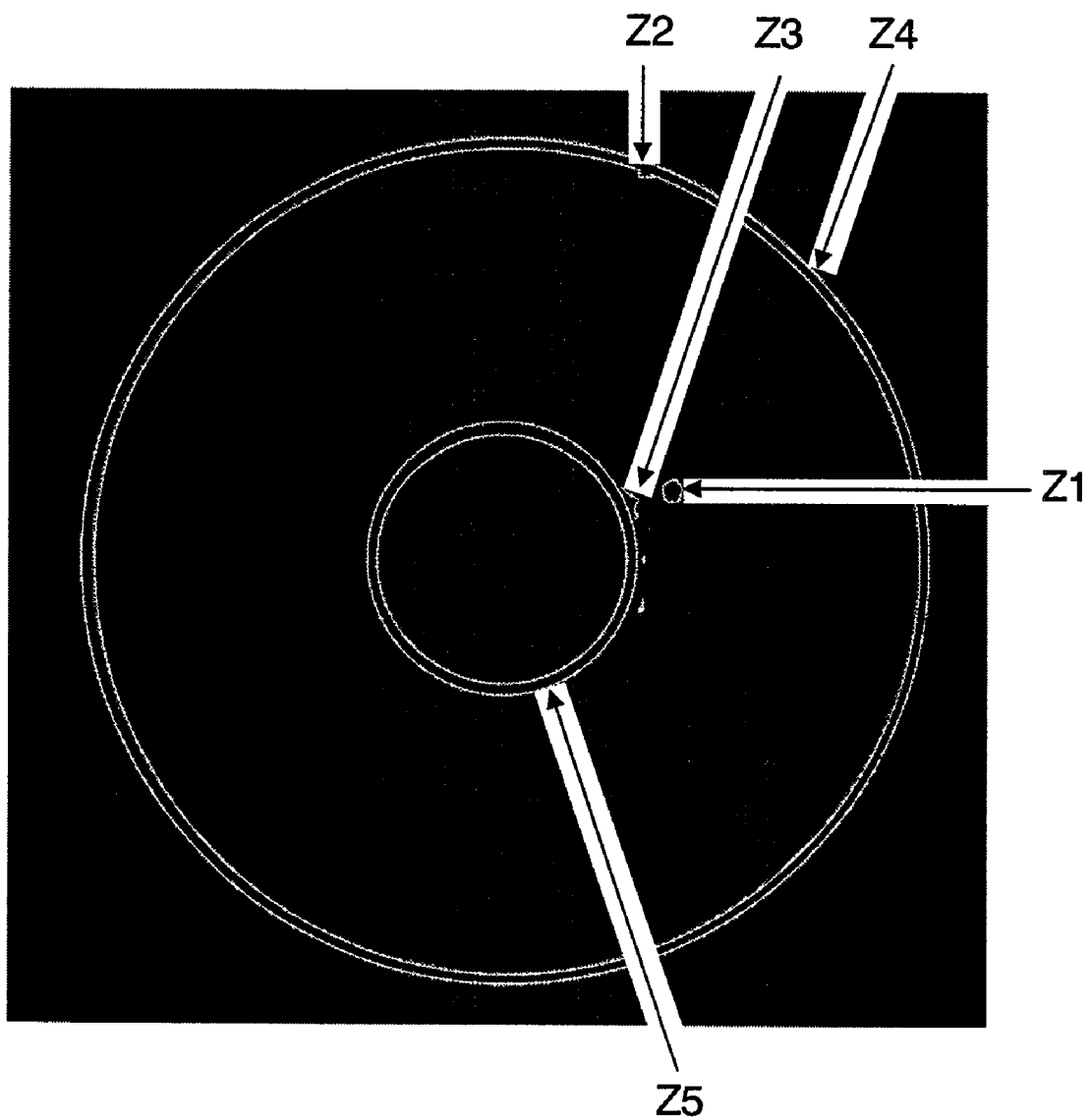
FIG. 5 is a figure displaying the image data edge-emphasized on the image data shown in FIG. 4, in the foreign matter inspection method on mirror-finished substrate according to embodiment 1 of the invention.
Figure 6:
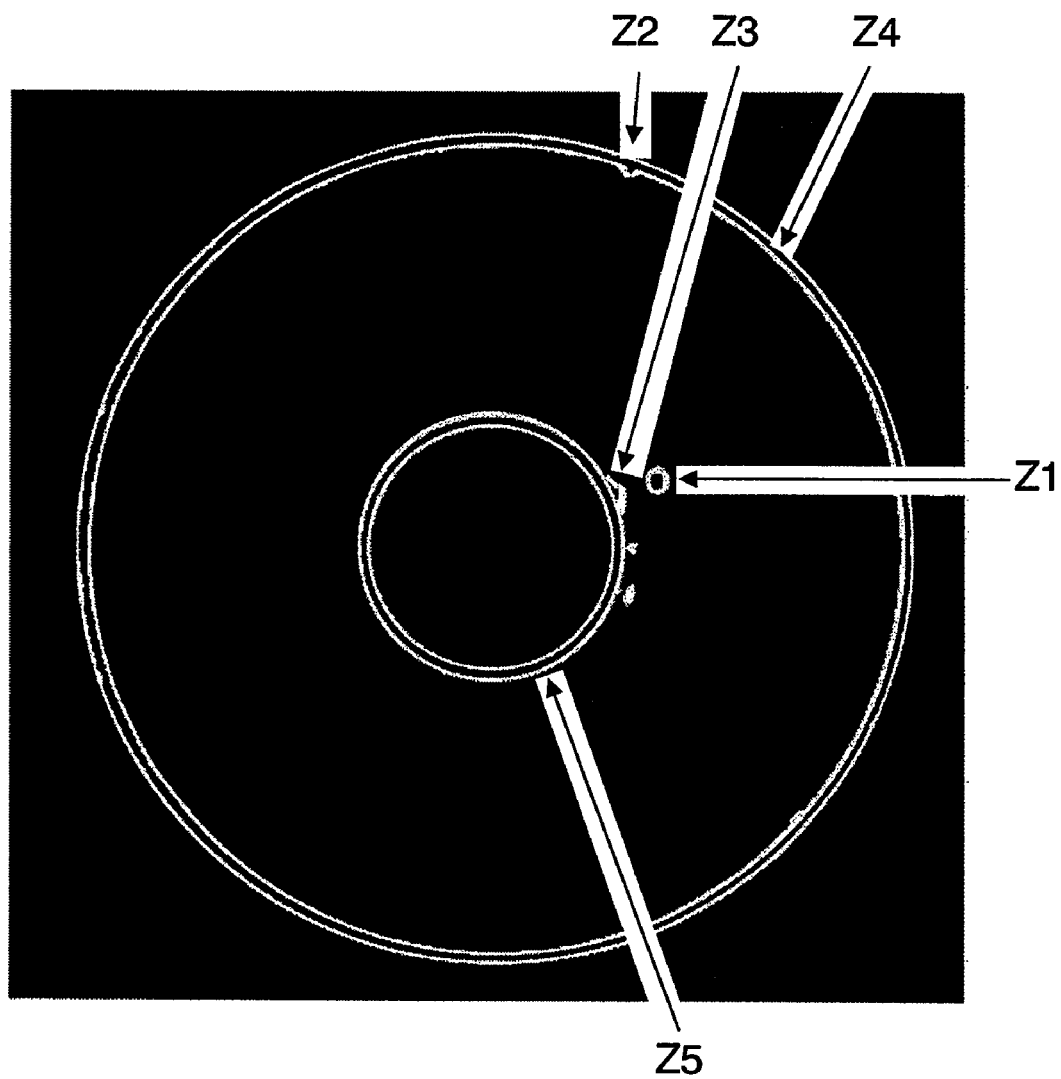
FIG. 6 is a figure displaying the edge-emphasized image data shown in FIG. 5 that is binarized and converted into binary data having light-region (in white) and dark-region data (in black), in the foreign matter inspection method on mirror-finished substrate according to embodiment 1 of the invention.
Figure 7:
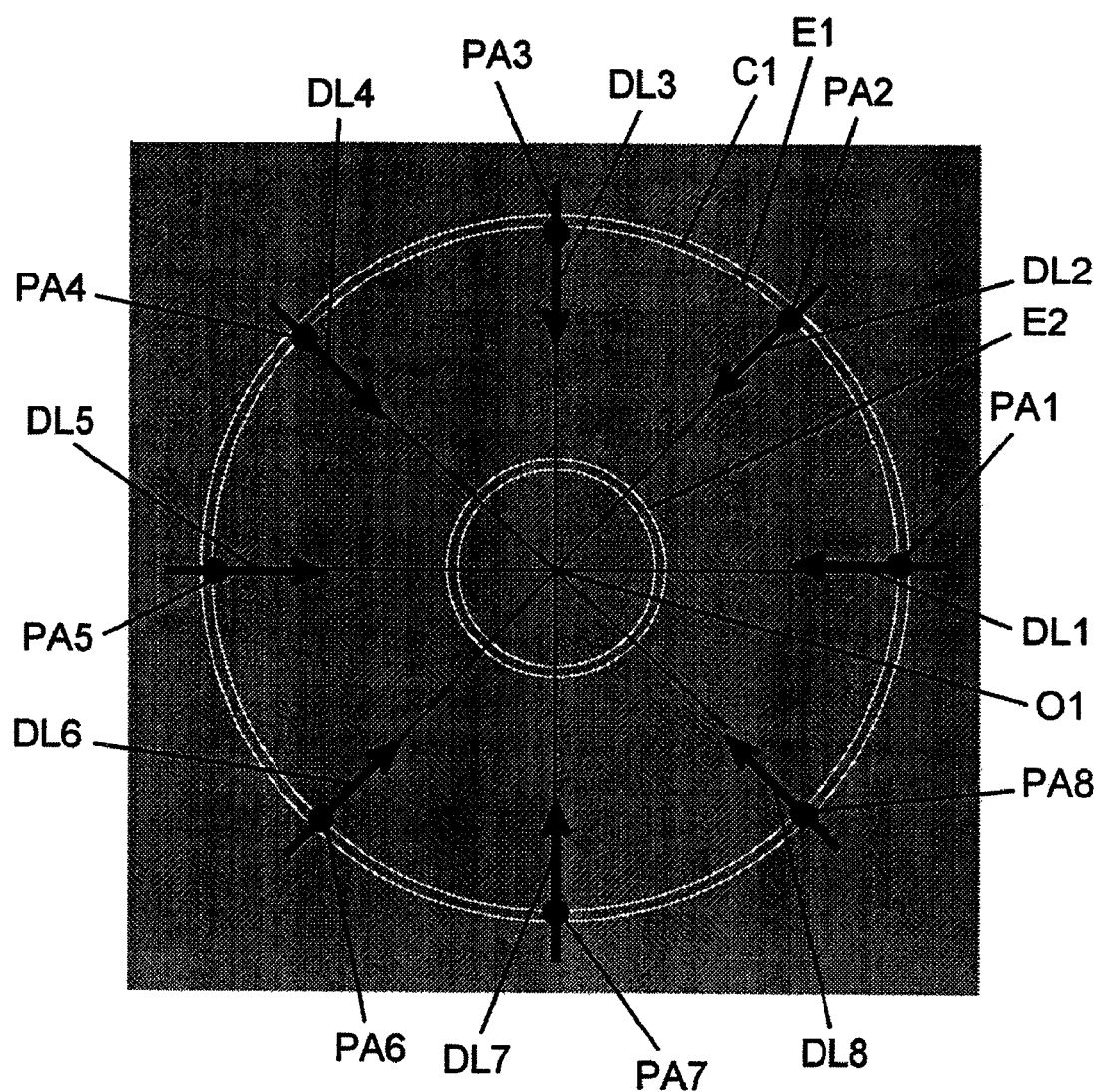
FIG. 7 is a figure explaining the estimation of an outer contour of an area to be inspected from the binary image shown in FIG. 6, in the foreign matter inspection method on mirror-finished substrate according to embodiment 1 of the invention.
Figure 8:
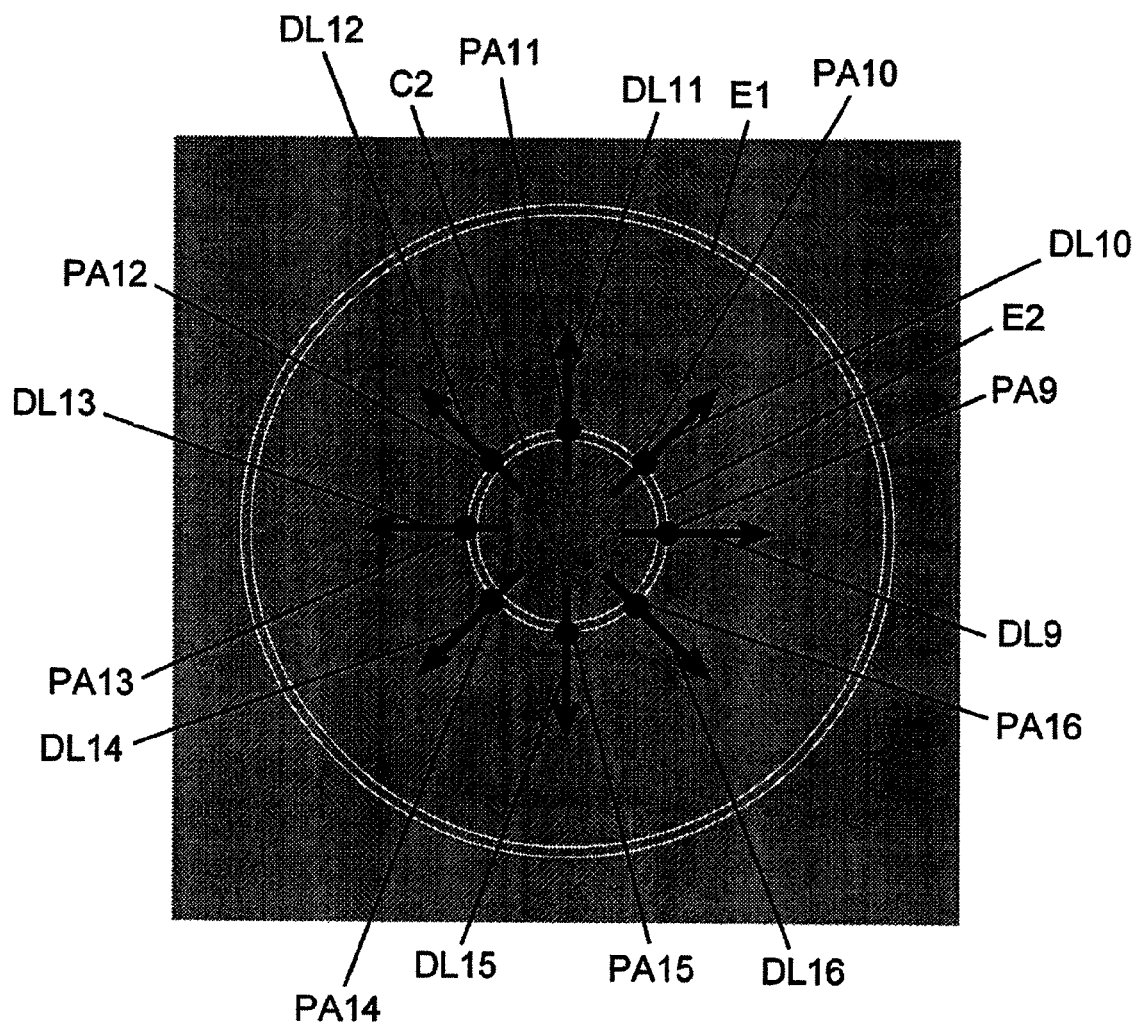
FIG. 8 is a figure explaining the estimation of an inner contour circle of the area to be inspected from the binary image obtained by binarization similarly to the estimation of an outer contour circle, in the foreign matter inspection method on mirror-finished substrate according to embodiment 1 of the invention.
Figure 9:
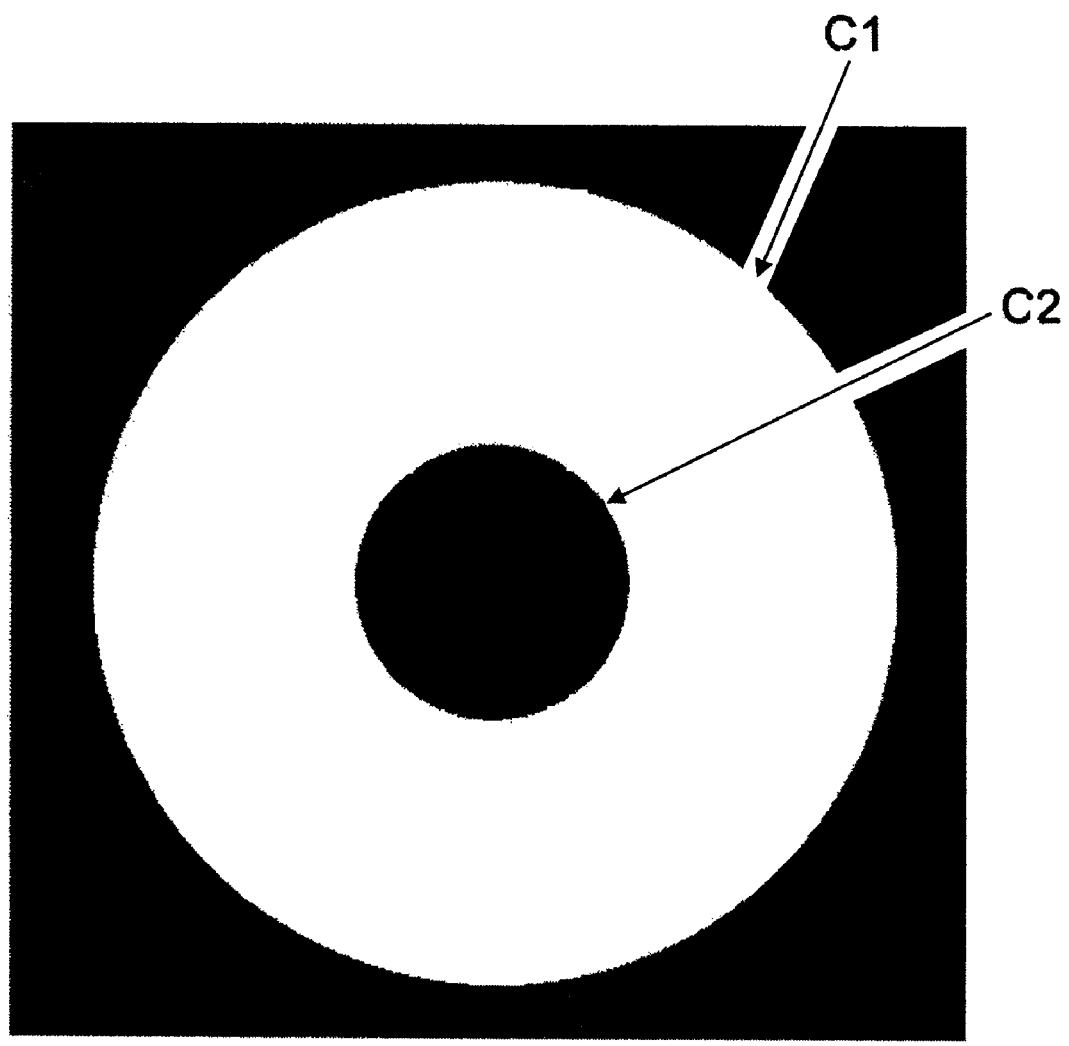
FIG. 9 is a figure showing a binary mask image generated by using the outer and inner contour circles estimated in the outer and inner contour estimations, in the foreign matter inspection method on mirror-finished substrate according to embodiment 1 of the invention.
Figure 10:
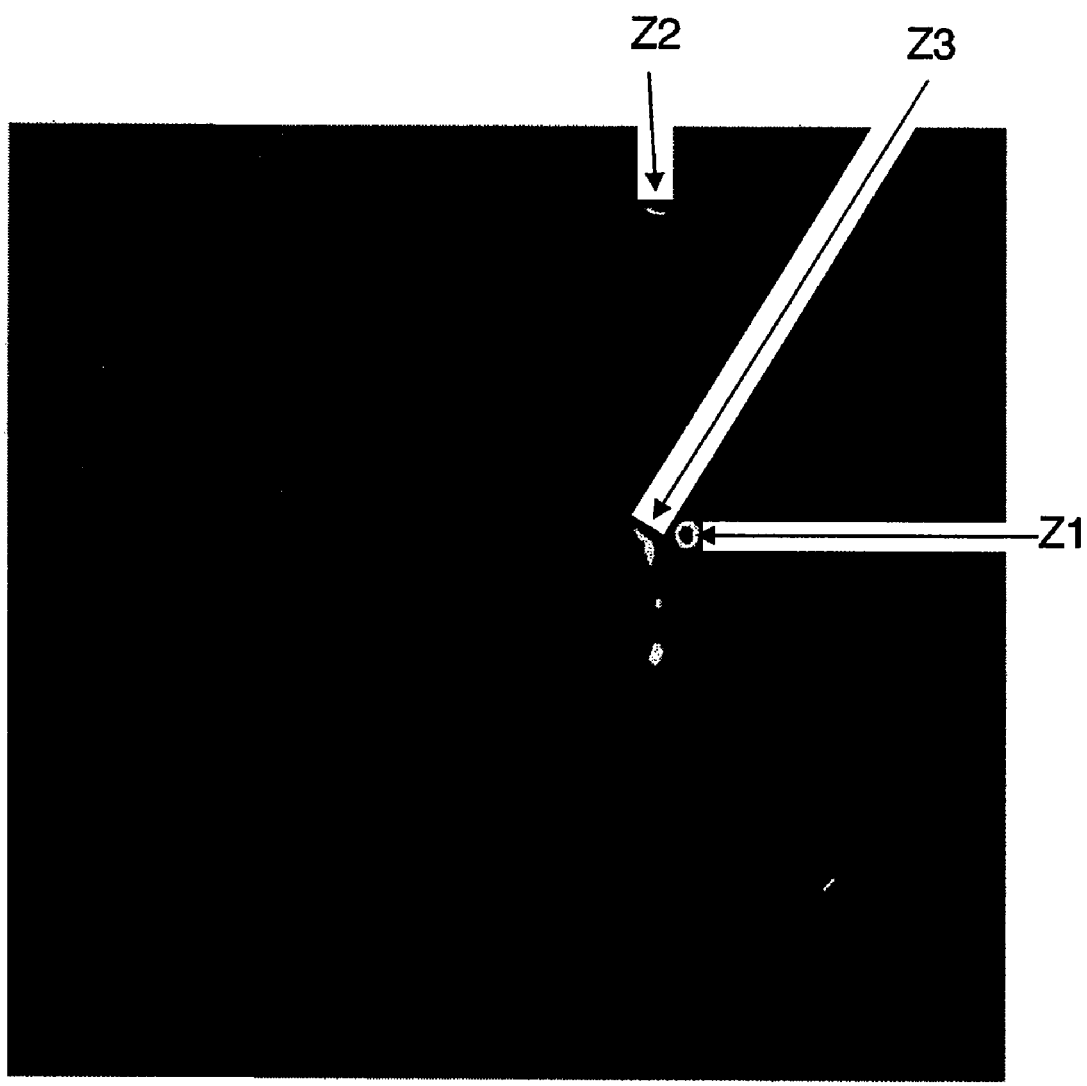
FIG. 10 is a figure showing the image data multiplied between the mask image data shown in FIG. 9 obtained by masking and the binary image data shown in FIG. 6 obtained by binarization, in the foreign matter inspection method on mirror-finished substrate according to embodiment 1 of the invention.
Figure 11:
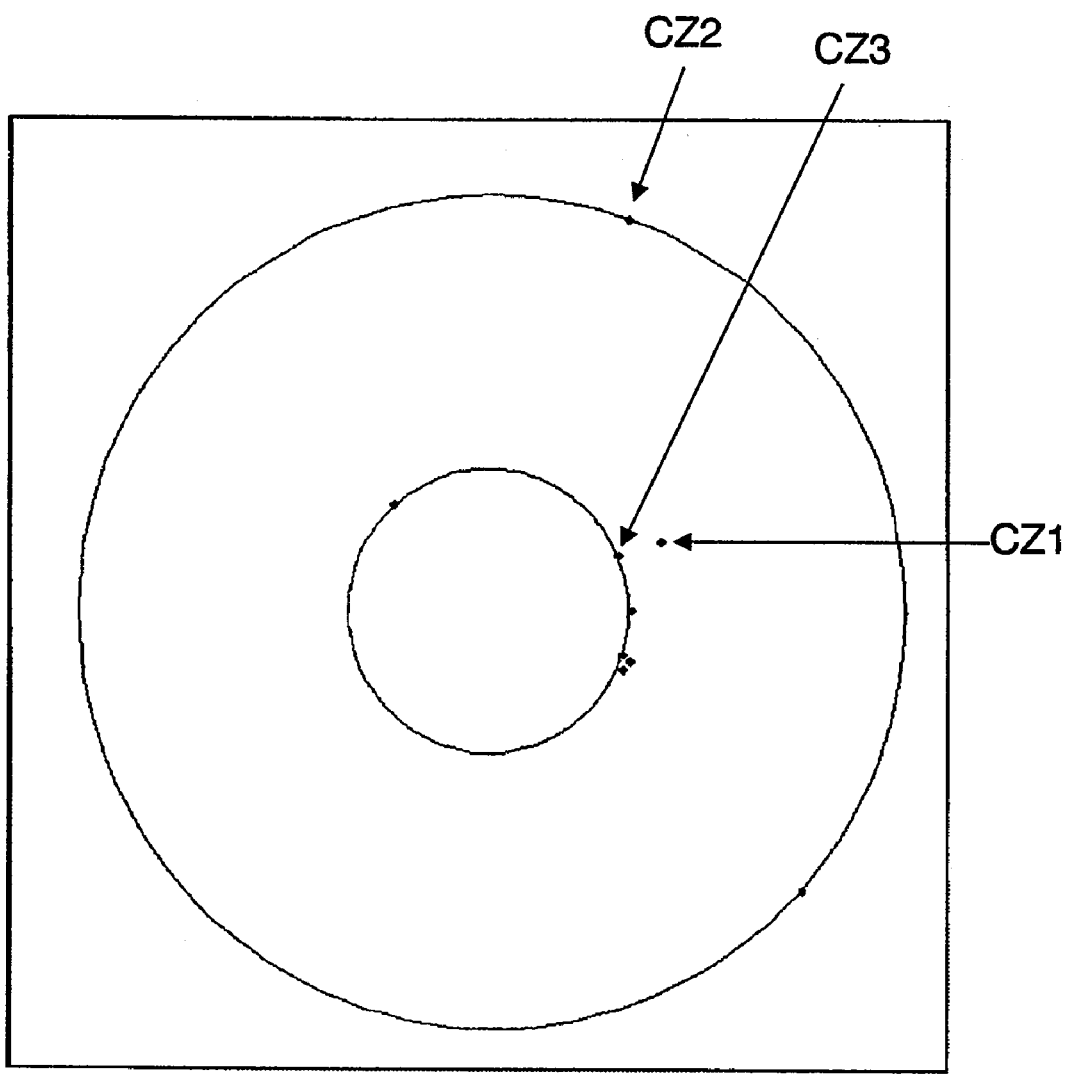
FIG. 11 is a figure that the coordinates of the foreign matters, extracted in foreign-matter extraction, are marked on a map, in the foreign matter inspection method on mirror-finished substrate according to embodiment 1 of the invention.

FIGS. 1 to 11 are figures explaining a foreign matter inspection method on mirror-finished substrate according to embodiment 1 of the present invention. FIG. 1 is a flowchart of the foreign matter inspection method on mirror-finished substrate according to embodiment 1 of the present invention. FIG. 2 is a schematic diagram of an inspection apparatus to be used in step ST1. FIG. 3 is a broken-away perspective view of a magnetic disk, for showing a relationship between illumination light and reflection light. FIG. 4 is a figure showing image data. FIG. 5 is a figure showing the image data emphasized at edges. FIG. 6 is a figure showing the image data processed with binarization. FIG. 7 is a plan view showing how to detect a sampling point at outer periphery. FIG. 8 is a plan view showing how to detect a sampling point at inner periphery. FIG. 9 is a figure showing mask image data. FIG. 10 is a figure showing the mask-treated image data. FIG. 11 is a map figure showing the coordinates of foreign matters.

Using FIG. 1, explanation is made on the procedure of the foreign-matter inspection method. At step ST1, prepared is gray-scaled two-dimensional image data that a magnetic disk 102, i.e. a substrate-under-inspection, has been taken an image at its contour.

At step ST 2, the two-dimensional image data is emphasized at edges. Namely, edge emphasis is made to enhance the image data in its portion where the data value changes sharply.

Furthermore, at step ST3, by binarization established with a predetermined threshold, the image data value exceeding the threshold is converted to a light-region data value (e.g. 1) while the image data value equal to or smaller than the threshold is to a dark-region data value (e.g. 0).

At step ST4, in outer-contour estimation, an outer contour is estimated of a foreign-matter inspection area from the binarized image data.

Furthermore, at step ST5, in inner-contour estimation, an inner contour is estimated of the foreign-matter inspection area from the binarized image data.

At step ST6, in mask treatment, a mask image is generated based on the contours estimated respectively in the outer and inner contour estimations, to clip a foreign-matter inspection area through the application of a mask to the binarized image data.

At step ST7, in foreign-matter detection, the data corresponding to a foreign matter is detected from the mask-treated image data. Furthermore, at step ST8, in map display, detected foreign matters are displayed at their sites on a map.

From now on, explanation is made on the process procedure of those steps.

FIG. 2 is a perspective view of an inspection apparatus for acquiring image data at step ST1 shown in FIG. 1. Imager device 9 is in a two-dimensional arrangement to obtain the image data of magnetic disk 102. Lens 10 is arranged on imager device 9. Imager device 9 is allowed to take an image broader in range than the inspection area of magnetic disk 102, a substrate under inspection. LED illuminator 11 is mounted, together with imager device 9 and lens 10, on lens barrel 12, to illuminate magnetic disk 102. On LED illuminator 11, a multiplicity of LEDs are arranged in a ring form to illuminate magnetic disk 102 in a surrounding manner. Lens 10 is adjusted to focus the image of magnetic disk 102, arranged on inspection stage 103, on imager device 9. The image signal, converted into an electric signal by imager device 9, is fetched in computer 109 and stored as image data in a memory of computer 109.

FIG. 3 is a broken-away perspective view for explaining the generation of image data in the inspection apparatus shown in FIG. 2. Magnetic disk 102 has mirror-finished surface 13 polished significantly smooth in order to record data thereon and chamfer 14 provided not to be readily broken at the edge thereof. Chamfer 14 is provided at both the outer and inner peripheral edges of magnetic disk 102.

In FIG. 3, illumination light L3 is light that is irradiated from LED illuminator 11 shown in FIG. 2 to magnetic disk 102. Regular-reflection light L4 is reflection light as reflected by mirror-finished surface 13. Irregular reflection light L5 arises where illumination light L3 is irregularly reflected by foreign matter 15 existing on mirror-finished surface 13 of magnetic disk 102 or irregularly reflected by chamfer 14.

In the inspection apparatus shown in FIG. 2, imager device 9 and LED illuminator 11 are positionally adjusted to introduce irregular reflection light L5 to imager device 9 without introducing regular-reflection light L4 to imager device 9. In the case no foreign matters exist on mirror-finished surface 13 of magnetic disk 102 at all, an image of chamfer 14 of magnetic disk 102 is reflected in the image obtained at imager device 9.

In the case foreign matter 15 is present on mirror-finished surface 13 of magnetic disk 102, irregular reflection light L5 is caused therefrom and guided by imager device 9 so that an image of foreign matter 15 is reflected in imager device 9. In this manner, foreign matter 15 can be detected that is present on mirror-finished surface 13 of magnetic disk 102.

FIG. 4 is a figure showing the image data of magnetic disk 102 acquired (step ST1) by use of the inspection apparatus explained in FIG. 2.

A plurality of foreign-matter images are reflected in the image data shown in FIG. 4, which are to be classified into three. Foreign-matter images Z1 to Z3 are shown as images representative of the respective groups. Reflection-upon-chamfer image Z4 is an image reflected upon the chamfer that is taken an image of the light irregularly reflected by outer peripheral chamfer 14 of magnetic disk 102 shown in FIG. 3. Meanwhile, reflection-upon-chamfer image Z5 is an image reflected upon the chamfer that is similarly taken an image of the light irregularly reflected by inner peripheral chamfer 14 of magnetic disk 102 shown in FIG. 3.

The image represented by foreign-matter image Z1 is observed as an independent bright point. The image represented by foreign-matter image Z2 is observed connected with reflection-upon-outer-chamfer image Z4. The image represented by foreign-matter image Z3 is observed connected with reflection-upon-inner-chamfer image Z5. The reason why the foreign-matter image represented by foreign-matter image Z2, Z3 is seen connected with the chamfer image is because the foreign matter is significantly close to or contacted with the edge of magnetic disk 102. Otherwise, it is because of an overlap between the irregular reflection light due to a foreign matter and the irregular reflection light due to the chamfer (FIG. 1, step ST1).

FIG. 5 is a figure displaying the image data that edge emphasis shown at step ST2 is done on the image data shown in FIG. 4. There is eliminated the halo due to stray light, etc.

as compared to the image shown in FIG. 4, thus clearly showing the boundary to chamfer 14 (images Z4, Z5) of magnetic disk 102 and the foreign matter 15 (images Z1, Z2, Z3). In (equation 1), (equation 2) and (equation 3), are shown operational expressions representative of the edge emphasis at step ST2.

$$P_{(i,j)} = \max \begin{bmatrix} |P_{(i+1,j-1)} - P_{(i-1,j-1)} + P_{(i+1,j)} - \\ P_{(i-1,j)} + P_{(i+1,j+1)} - P_{(i-1,j+1)}|, \\ |P_{(i-1,j+1)} - P_{(i-1,j-1)} + P_{(i,j+1)} - \\ P_{(i,j-1)} + P_{(i+1,j+1)} - P_{(i+1,j-1)}| \end{bmatrix} \quad \text{Equation 1}$$

$$P_{(i,j)} = \max \begin{bmatrix} |P_{(i+1,j-1)} - P_{(i-1,j-1)} + 2P_{(i+1,j)} - \\ 2P_{(i-1,j)} + P_{(i+1,j+1)} - P_{(i-1,j+1)}|, \\ |P_{(i-1,j+1)} - P_{(i-1,j-1)} + 2P_{(i,j+1)} - \\ 2P_{(i,j-1)} + P_{(i+1,j+1)} - P_{(i+1,j-1)}| \end{bmatrix} \quad \text{Equation 2}$$

If $|P_{(i,j)} - M_{(i,j)}| > S_{(i,j)}$, then    Equation 3

$P_{(i,j)} = P_{(i,j)}$.

If $|P_{(i,j)} - M_{(i,j)}| \leq S_{(i,j)}$, then $P_{(i,j)} = M_{(i,j)}$.

Here, $M_{(i,j)} = \frac{1}{9}(P_{(i-1,j-1)} + P_{(i,j-1)} + P_{(i+1,j-1)} + P_{(i-1,j)} + P_{(i,j)} + P_{(i+1,j)} + P_{(i-1,j+1)} + P_{(i,j+1)} + P_{(i+1,j+1)})$ $S^2_{(i,j)} = \frac{1}{9}(P^2_{(i-1,j-1)} + P^2_{(i,j-1)} + P^2_{(i+1,j-1)} + P^2_{(i-1,j)} + P^2_{(i,j)} + P^2_{(i+1,j)} + P^2_{(i-1,j+1)} + P^2_{(i,j+1)} + P^2_{(i+1,j+1)}) - M^2_{(i,j)}$ In (equation 1), (equation 2) and (equation 3), symbol "i" represents the arrangement order of pixels of two-dimensional image data with respect to the X direction while symbol "j" the arrangement order thereof with respect to the Y direction. Symbol "P" represents light-intensity value. Accordingly, light-intensity value P(i,j) represents a light-intensity value, of the pixel of the two-dimensional image data, that is i-th with respect to the X direction and j-th with respect to the Y direction.

The expressions of (equation 1), (equation 2) and (equation 3) represent to arithmetically determine a light-intensity value P(i,j) of a desired one pixel of the image-processed two-dimensional image data shown in the left-side member according to the right-side expression by use of the light-intensity values P(i,j), P(i+1,j), etc. of a plurality of pixels of the former (pre-process) two-dimensional image data associated therewith by means of the relevant symbols "i" and "j".

Brief explanation is made below on the arithmetic operation of the equations. The arithmetic operation in the right-side members of (equation 1) and (equation 2) represents to employ the greater one of two term's value (absolute values) segmented by in-parenthesis commas, i.e. of the upper and lower terms.

In (equation 3), M(i,j) represents a mean value over a desired pixel and its peripheral pixels of the pre-process two-dimensional image data represented by arrangement order (i,j). S(i,j) is a deviation value over a desired pixel and its peripheral pixels of the pre-process two-dimensional image data represented by arrangement order (i,j).

In (equation 3), when the absolute value of a difference, between the light-intensity value P(i,j) of a desired pixel of the pre-process two-dimensional image data and the mean light-intensity value M(i,j) over the desired pixel and its peripheral pixel, is greater than deviation value S(i,j), the post-process light-intensity value P(i,j) is made equal to pre-process light-intensity value P(i,j). Meanwhile, when the absolute value of a difference, between light-intensity value P(i,j) of a desired pixel of the pre-process two-dimensional image data and the mean light-intensity value M(i,j) over the desired pixel and its peripheral pixel, is equal to or smaller than deviation value S(i,j), post-process light-intensity value P(i,j) is made as the mean value M(i,j) of the pre-process light-intensity values in the periphery thereof.

Those arithmetic operations each serve as a high-pass filter that absorbs the low-range component of image light-intensity change. By removing the light-intensity changing components comparatively moderate such as halo, sharp light-intensity change can be emphasized at foreign matter 15 or chamfer 14 (FIG. 1, step ST2).

FIG. 6 is a figure displaying the image data edge-emphasized as shown in FIG. 5 is binarized into binary data having light-region data (in white) and dark-region data (in black) (FIG. 1, step ST3).

In FIG. 6, the area, surrounded by outer contour E1 and inner contour E2 of mirror-finished surface 13 of magnetic disk 102, provides an area to be inspected, i.e. inspection area. In the inspection area, foreign-matter images are to be detected (FIG. 1, step ST3).

FIG. 7 is a figure for explaining the estimation of an outer contour of an inspection area from the binary image shown in FIG. 6 (see FIG. 1, step ST4). In FIG. 7, as shown by directional line DL1, a sampling direction at outer periphery is defined to sequentially inspect data in a manner crossing the outer peripheral edge of magnetic disk 102 in a direction of from the outer to inner periphery thereof, thereby conducting an inspection of image data. In the inspection of image data, there appears two points where data changes in value from dark-region data to light-region data, the second point of which is at the boundary of between mirror-finished surface 13 and chamfer 14 closer to the outer peripheral edge. Thus, the relevant point is registered as outer-contour sampling point PA1. Likewise, by establishing sampling directions at outer periphery as given by directional lines DL2-DL8, outer-contour sampling points PA2-PA8 are detected and registered. Because the substrate under inspection is magnetic disk 102, the outer contour is circular whose outer-contour circle C1 can be estimated from outer-contour sampling points PA1-PA8 registered. To estimate outer-contour circle C1 on the basis of outer-contour sampling points PA1-PA8 registered, least-square error method is used. The least-square error method is a method that, provided that the outer-contour sampling points are respectively at coordinates (Xn, Yn) and the circle to estimate has a center (Xc, Yc) with a radius R, estimation is made for Xc, Yc, R in a manner minimizing the square error Δ shown in (equation 4) (step ST4 in FIG. 1).

$$\Delta = \sum_n \left[ \sqrt{(X_n - X_c)^2 + (Y_n - Y_c)^2} - R \right]^2 \quad \text{Equation 4}$$

In this case, in accordance with the shape of the substrate under inspection, a point nearby the center of gravity, for example, of the shape is established as a temporary center O1, to establish an X-Y coordinate having a coordinate origin at center O1. By taking outer-contour sampling points at points on straight lines radially extending from center O1, coordinates (Xn, Yn) (n=1-8, in the embodiment) are respectively detected as to those.

In embodiment 1, because the substrate-under-inspection is magnetic disk 102 having a center bore, it is in a ring form as known whose outer contour is circular. Accordingly, the respective coordinates (Xn, Yn) of outer-contour sampling points PA1-PA8 can be detected as coordinates on the X-Y coordinate set up, as its origin, with the assumed center O1 of magnetic disk 102. From coordinates (Xn, Yn) thus detected, center (Xc, Yc) and radius R of outer contour circle C1 can be determined according to (equation 4).

FIG. 8 is a figure for explaining the estimation of an inner contour circle in an area to be inspected from the binary image obtained by binarization at step ST3 (step ST5) similarly to the estimation of an outer contour circle. In FIG. 8, as shown in directional line DL9, a sampling direction at inner periphery is defined to sequentially inspect data in a manner crossing the inner peripheral edge of magnetic disk 102 in a direction of from the inner to outer periphery thereof, thereby conducting an inspection of image data.

Two points appear where data changes in value from dark-region data to light-region data, the second point of which is at the boundary of between mirror-finished surface 13 and chamfer 14 closer to the inner peripheral edge. Thus, the relevant point is registered as inner-contour sampling point PA9. Likewise, by establishing sampling directions at outer periphery as given at directional lines DL10-DL16, outer-contour sampling points PA10-PA16 are detected and registered. Inner contour circle C2 is estimated by use of the least-square error method similarly to estimation of outer contour circle C1, on the basis of the coordinates of inner-contour sampling points PA9-PA16 registered (FIG. 1, step ST5). Estimating inner contour circle C2 is similar to estimating outer contour circle C1, and hence omitted to explain.

FIG. 9 is a figure showing a binary mask image generated by using outer and inner contour circles Cl, C2 respectively estimated in the outer and inner contour estimations. The area, inner than outer contour circle C1 and outer than inner contour circle C2, is provided with a light-region data value (in white) while the other area is with a dark-region data value (in black). The area shown by the light-region data value provides an inspection area (FIG. 1, step ST6).

FIG. 10 is a figure showing the image data that the FIG. 9 mask image data obtained by masking 6 is multiplied with the FIG. 6 binary image data obtained by the binarization step ST3. Namely, light-region data is provided only by the overlap area between the light-region data of the mask image data and the light-region data of the binary image data. In FIG. 10 image data, there are erased the images of the other regions than mirror-finished surface 13 of magnetic disk 102, e.g. outer contour E1 and inner contour E2 in FIG. 6 wherein a foreign matter or projection, existing in the inspection area on mirror-finished surface 13 of magnetic disk 102, remains as an image portion having a light-region data value (in white). Foreign-matter images, contacting with outer or inner contour E1, E2, e.g. foreign-matter images Z2, Z3, are provided as images that are independent in the foreign-matter image portions thereof (FIG. 1, step ST7).

Foreign-matter detecting step ST7 is a process to extract a lump of image (e.g. Z1-Z3) having a light-region data value from the image processed as shown in FIG. 10.

FIG. 11 is a figure that the foreign matter extracted in foreign-matter detection 7 is marked in coordinate on a map (FIG. 1, step ST8). Namely, foreign-matter's coordinates are indicated as spots CZ1, CZ2 and CZ3 correspondingly to foreign-matter images Z1, Z2 and Z3 shown in FIG. 4. The other foreign-matter images, not given with reference symbols, are also indicated as spots.

As described above, embodiment 1 is a method to detect a foreign matter by clipping out only a foreign matter on mirror-finished surface 13 through estimating an area of mirror-finished surface 13 to be inspected as outer and inner contour circles C1, C2 from binary image data which magnetic disk 102 is entirely captured, and applying a mask to the outer of outer contour circle C1 and the inner of inner contour circle C2. Accordingly, as in the foregoing prior art, there is no need of such an expensive measuring instrument such as a laser dimension-measuring instrument to correctly measure the outer peripheral edge position of a disk. Meanwhile, the use of the method of embodiment 1 makes it possible to clearly clip even a foreign-matter image, significantly in proximity to or in contact with chamfer 14 of magnetic disk 102, out of the image of chamfer 14. Thus, it can be detected as a foreign matter by a simple process.

In embodiment 1, outer-contour sampling points PA1-PA8 were detected by sequentially inspecting image data in a direction of from the periphery to center of the image. Conversely, the image data may be inspected sequentially in a direction of from the center to periphery of the image. In this case, the first point, of among points where value changes from dark-region data to light-region data, provides a boundary between mirror-finished surface 13 and chamfer 14 closer to the outer edge.

Likewise, inner-contour sampling points PA9-PA16 were detected by sequentially inspecting image data in a direction of from the center to periphery of the image. Conversely, the image data may be inspected sequentially in a direction of from the periphery to center of the image. In this case, the first point, of among points where value changes from dark-region data to light-region data, provides a boundary between mirror-finished surface 13 and chamfer 14 closer to the inner edge, similarly to the detection of outer-contour sampling points PA1-PA8.

In embodiment 1, outer-contour sampling points and inner-contour sampling points are both taken eight in the number. In the case of a circle, sampling points may be three in the number in minimum or approximately twenty in the number. Where sampling points are excessively smaller in the number, shape estimation error increases. Meanwhile, where sampling points are excessively greater in the number, estimation accuracy does not improve despite taking an operation time. It is accordingly important to select a proper number of sampling points in accordance with a form to estimate. As indicated in embodiment 1, nearly six to twenty points are desired where the shape to estimate is a circle.

In embodiment 1, the substrate-under-inspection was as a magnetic disk having a center hole. Alternatively, it may be a mirror-finished substrate not having a center hole like a silicon substrate for use in semiconductor manufacture. In the case of a mirror-finished substrate not having a center hole, it is naturally satisfactory to detect a coordinate of an outer-contour sampling point wherein no inner-contour sampling points exist.

The invention is not limited to a circular substrate in outer shape but may be triangular, square or the like, i.e. applicable to any form provided that the geometric shape has a contour to be defined reduced in size. Where the substrate-under-inspection is polygonal for example, a point nearby a center-of-gravity of the shape is established as a virtual center, which center is taken as a coordinate origin to thereby set up an X-Y coordinate. Outer-contour sampling points are taken on straight lines radially extending from the center (coordinate origin), to detect respective coordinates of outer-contour sampling points.

It can be recognized whether the substrate-under-inspection is triangular, square or polygonal in form, by observing the substrate-under-inspection. This makes it possible to recognize that the detected one of outer-contour sampling points exists on which one of the sides constituting a polygon forming the outer contour. Accordingly, from a plurality of outer-contour sampling points existing on one side forming an outer-contour of the substrate-under-inspection, an equation on the X-Y coordinate can be estimated as to the straight line forming the relevant one side. In estimating an equation for the straight line representing the one side forming the contour line, the least-square error method may be used so as to minimize the square sum of the distances between the straight line and the outer-contour sampling points. By thus using the least-square error method for the outer-contour sides of the substrate-under-inspection, equations are determined correspondingly to the respective straight lines of the sides. The region surrounded by the straight lines is satisfactorily provided as an inspection area. Accordingly, by detecting respective coordinates of outer-contour sampling points, inspection area can be estimated for the subject to be inspected. Meanwhile, by the processes shown in FIG. 1, a foreign-matter or projection coordinate in the inspection area can be marked on a map.

As described above, according to embodiment 1, foreign-matter detection is to be implemented by estimating an inspection area with use of the image data where the contour of the inspection area of the substrate-under-inspection has been taken an image and applying a mask to the image data in an area other than the inspection area, followed by multiplying binarized image data and mask image data together. Consequently, inspection is possible to conduct thoroughly throughout the entire surface of the inspection area. Moreover, because even the image of a foreign matter or projection in proximity to or in contact with the contour of the inspection area can be clearly separated from the image of inspection-region contour, a foreign matter or projection existing nearby the contour can be detected positively.

Embodiment 2

Figure 12:
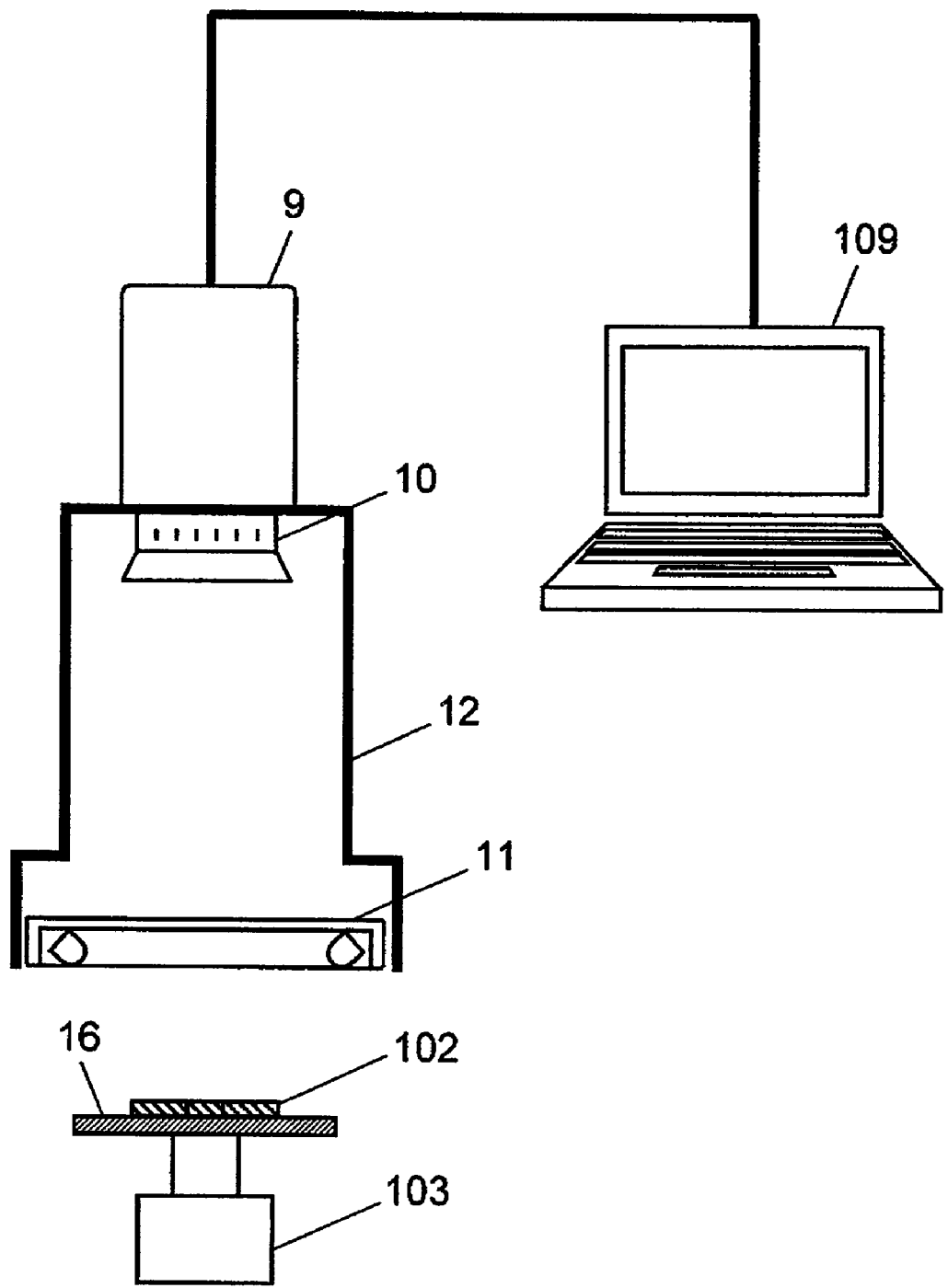
FIG. 12 is a schematic diagram of an inspection apparatus for use in a foreign matter inspection method on mirror-finished substrate according to embodiment 2 of the invention.
Figure 13:
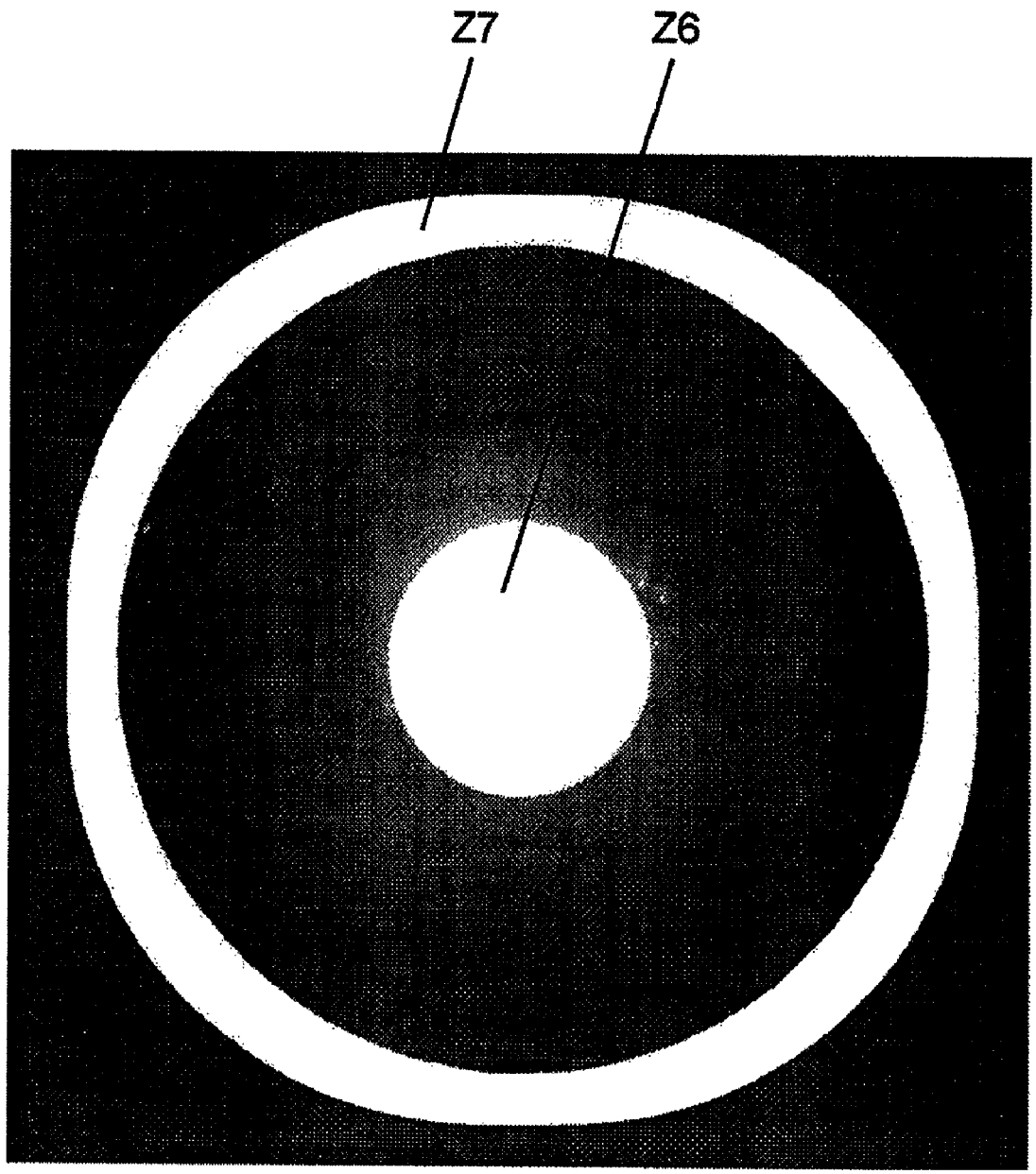
FIG. 13 is a figure showing the image data acquired by the inspection apparatus for use in the foreign matter inspection method on mirror-finished substrate according to embodiment 2 of the invention.
Figure 14:
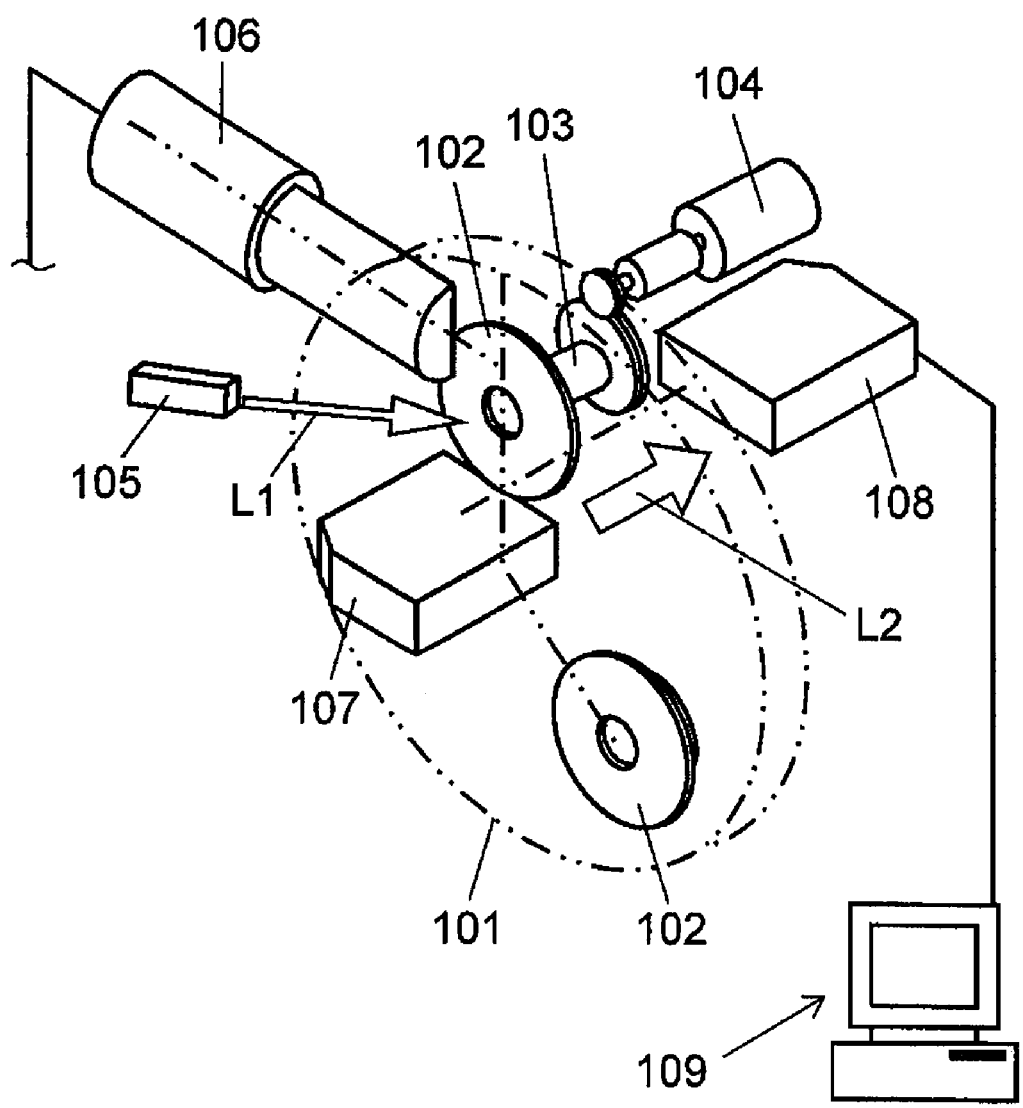
FIG. 14 is a schematic diagram of an inspection apparatus for use in a foreign matter inspection method on mirror-finished substrate on the conventional foreign matter inspection apparatus.

FIG. 12 is a schematic diagram of an inspection apparatus for explaining a foreign matter inspection method on mirror-finished substrate according to embodiment 2 of the present invention. FIG. 13 is a figure showing the image data obtained by the relevant inspection apparatus.

In FIG. 12, irregular reflection plate 16 is to irregularly reflect the illumination light of from LED illuminator 11. The inspection apparatus of embodiment 2 differs from embodiment 1 in that magnetic disk 102 is rested on irregular reflection plate 16. The others are identical to the inspection apparatus of embodiment 1, and hence omitted to explain.

FIG. 13 is a figure showing the image data acquired by the inspection apparatus shown in FIG. 12. Irregular-reflection-plate images Z6, Z7 are captured by introducing the reflection light upon irregular reflection plate 16 to imager device 9. By thus providing irregular reflection plate 16, contours of mirror-finished surface 13 of magnetic disk 102 are displayed clearly even where a chamfer 14 does not exist in magnetic disk 102 or it is significantly small, thus making it possible to clip and inspect image data only of mirror-finished surface 13 serving as an inspection surface.

By variously processing the image data obtained with use of the inspection apparatus as image data of a flowchart shown in FIG. 1 according to embodiment 1, inspection can be conducted thoroughly throughout the entire inspection area of the substrate-under-inspection, making it possible to positively detect a foreign matter or projection in the inspection area. The processing at each step is similar to embodiment 1, and hence omitted to explain. In the processing at each step to estimate an outer or inner contour of the inspection area, the point where data value changes from dark-region data to light-region data appears only one in the number. Accordingly, in embodiment 2, the respective points where dark-region data changes to light-region data obtained in the outer-contour and inner-contour estimations each provide boundaries of mirror-finished surface 13 to outer-edge side chamfer 14 and to inner-edge side chamfer 14.

Incidentally, effect is similarly available if providing a spontaneous emission plate buried with lamps or LEDs in place of irregular reflection plate 16.

As described above, according to embodiment 2, effect is available similarly to embodiment 1. Even where a chamfer is not existent or is significantly small in the outer or inner peripheral edge, the contour of the mirror-finished surface is to be clearly displayed that is an inspection area on the substrate-under-inspection. The image data only of the mirror-finished surface, forming an inspection surface, can be clipped out for inspection, thus enabling foreign-matter inspection with significant accuracy.

INDUSTRIAL APPLICABILITY

The foreign matter inspection method on mirror-finished substrate according to the invention is useful as a method to inspect a dust or projection put on a magnetic disk for use on a hard disk drive. Particularly because inspection is available thoroughly throughout the entire mirror-finished region of a magnetic disk, it is useful in inspecting a foreign matter on a magnetic disk before magnetic transfer where to transfer a signal through magnetic transfer by placing the master disk in contact with the magnetic disk. Besides, because of usefulness as a foreign-matter inspection method for inspecting the presence/absence of a dust or a defect put on a substrate having a mirror-finished surface, e.g. a silicon wafer, a photomask substrate or the like for use in semiconductor manufacture, industrial applicability is available high.

The invention claimed is:

1. A method for inspecting foreign matter on a mirror-finished substrate-under-inspection, comprising:
   emitting illumination light to the substrate-under-inspection;
   obtaining image data based on an image which includes irregular reflection light that has been irregularly reflected from the substrate-under-inspection;
   performing arithmetic operation, using a microprocessor, based on either one of operational expressions given in (equation 1), (equation 2) or (equation 3) provided that a light-intensity value of a desired one pixel of the image data as P(i, j) (where "i", "j": an integer for specifying a desired position wherein "i" indicates an arrangement order in a direction of X-axis while "j" indicates an arrangement order in a direction of Y-axis), a mean value over a desired pixel and its peripheral pixels of the image data as M(i, j) and a deviation value over a desired pixel and its peripheral pixels of the image data as S(i, j), $$P_{(i,j)} = \max \begin{bmatrix} |P_{(i+1,j-1)} - P_{(i-1,j-1)} + P_{(i+1,j)} - \\ P_{(i-1,j)} + P_{(i+1,j+1)} - P_{(i-1,j+1)}|, \\ |P_{(i-1,j+1)} - P_{(i-1,j-1)} + P_{(i,j+1)} - \\ P_{(i,j-1)} + P_{(i+1,j+1)} - P_{(i+1,j-1)}| \end{bmatrix} \quad \text{Equation 1}$$

(where right-side operation represents to employ the greater one of two term's values (absolute value) segmented by an in-bracket commas, i.e. of the upper and lower terms)

$$P_{(i,j)} = \max \begin{bmatrix} |P_{(i+1,j-1)} - P_{(i-1,j-1)} + 2P_{(i+1,j)} - \\ 2P_{(i-1,j)} + P_{(i+1,j+1)} - P_{(i-1,j+1)}|, \\ |P_{(i-1,j+1)} - P_{(i-1,j-1)} + 2P_{(i,j+1)} - \\ 2P_{(i,j-1)} + P_{(i+1,j+1)} - P_{(i+1,j-1)}| \end{bmatrix} \quad \text{Equation 2}$$

(where right-side operation represents to employ the greater one of two term's values (absolute value) segmented by an in-bracket commas, i.e. of the upper and lower terms), If $|P_{(i,j)} - M_{(i,j)}| > S_{(i,j)}$, \hfill Equation 3 then $P_{(i,j)} = P_{(i,j)}$.

If $|P_{(i,j)} - M_{(i,j)}| < S_{(i,j)}$, then $P_{(i,j)} = M_{(i,j)}$.

Here, $M_{(i,j)} = \frac{1}{9}(P_{(i-1,j-1)} + P_{(i,j-1)} + P_{(i+1,j-1)} + P_{(i-1,j)} + P_{(i,j)} + P_{(i+1,j)} + P_{(i-1,j+1)} + P_{(i,j+1)} + P_{(i+1,j+1)})$ $S^2_{(i,j)} = \frac{1}{9}(P^2_{(i-1,j-1)} + P^2_{(i,j-1)} + P^2_{(i+1,j-1)} + P^2_{(i-1,j)} + P^2_{(i,j)} + P^2_{(i+1,j)} + P^2_{(i-1,j+1)} + P^2_{(i,j+1)} + P^2_{(i+1,j+1)}) - M^2_{(i,j)}$ detecting coordinates of a plurality of contour sampling points indicative of a contour of an inspection area from the image data;

estimating the inspection area from the coordinates of the plurality of contour sampling points;

preparing mask image data where masking is applied to an area other than the inspection area by use of the image data the image-processing has been done; and performing foreign-matter detection on the image data by using the mask image data.

2. The method of claim 1, wherein the image data, where the contour of the inspection area of the substrate-under-inspection has been taken an image, is binary image that binarization has been done.

3. The method of claim 1, wherein the contour line is estimated so as to minimize a square sum of distances between coordinates of the plurality of contour sampling points and the contour line of the inspection area of the substrate-under-inspection.

4. The method of claim 1, wherein a reflection member that has been irregularly reflective of light or a light-emission member for emitting light spontaneously is provided in a neighborhood of the substrate-under-inspection, and the image data being produced such that an image of the reflection member or light-emission member is displayed in a background of the substrate-under-inspection, in the image data where an area broader than the inspection area of the substrate-under-inspection has been taken an image.

5. The method of claim 2, wherein the contour line is estimated so as to minimize a square sum of distances between coordinates of the plurality of contour sampling points and the contour line of the inspection area of the substrate-under-inspection.

6. The method of claim 2, wherein a reflection member that has been irregularly reflective of light or a light-emission member for emitting light spontaneously is provided in a neighborhood of the substrate-under-inspection, and the image data being produced such that an image of the reflection member or light-emission member is displayed in a background of the substrate-under-inspection, in the image data where an area broader than the inspection area of the substrate-under-inspection has been taken an image.

\* \* \* \* \*

UNITED STATES PATENT AND TRADEMARK OFFICE
CERTIFICATE OF CORRECTION

PATENT NO. : 8,055,055 B2  
APPLICATION NO. : 11/911594  
DATED : November 8, 2011  
INVENTOR(S) : Taizou Hamada et al.

Page 1 of 1

It is certified that error appears in the above-identified patent and that said Letters Patent is hereby corrected as shown below:

Column 15, line 26, "<S" should read --≤S--

Signed and Sealed this
Twentieth Day of March, 2012

David J. Kappos
*Director of the United States Patent and Trademark Office*